United States Patent
Charlier De Chily et al.

(10) Patent No.: US 9,139,504 B2
(45) Date of Patent: *Sep. 22, 2015

(54) LANOLIN SUBSTITUTE, PRODUCTION METHOD THEREOF AND APPLICATIONS OF SAME

(71) Applicant: ALDIVIA SA, Saint-Genis Laval (FR)

(72) Inventors: Pierre Charlier De Chily, Irigny (FR); Mikaele Raynard, Villeurbanne (FR)

(73) Assignee: ALDIVIA SA, Saint-Genis Laval (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/755,598

(22) Filed: Jan. 31, 2013

(65) Prior Publication Data

US 2013/0224138 A1    Aug. 29, 2013

Related U.S. Application Data

(62) Division of application No. 10/481,890, filed as application No. PCT/FR02/02271 on Jun. 28, 2002, now Pat. No. 8,420,842.

(30) Foreign Application Priority Data

Jul. 2, 2001 (FR) ...................................... 01 08905

(51) Int. Cl.
| | |
|---|---|
| C07C 51/00 | (2006.01) |
| A61K 8/00 | (2006.01) |
| A61K 8/18 | (2006.01) |
| A61K 8/02 | (2006.01) |
| A61K 31/20 | (2006.01) |
| A23D 9/00 | (2006.01) |
| A61Q 1/04 | (2006.01) |
| C07C 57/02 | (2006.01) |
| A61K 8/31 | (2006.01) |
| A61K 8/92 | (2006.01) |
| A61K 9/00 | (2006.01) |
| A61K 9/107 | (2006.01) |
| A61K 47/44 | (2006.01) |
| A61Q 1/06 | (2006.01) |
| A61Q 19/00 | (2006.01) |
| C09D 11/00 | (2014.01) |
| C09G 1/14 | (2006.01) |
| C10M 159/12 | (2006.01) |
| C11C 3/00 | (2006.01) |
| C11C 3/02 | (2006.01) |
| C14C 9/02 | (2006.01) |

(52) U.S. Cl.
CPC . *C07C 57/02* (2013.01); *A61K 8/31* (2013.01); *A61K 8/922* (2013.01); *A61K 9/0014* (2013.01); *A61K 9/107* (2013.01); *A61K 47/44* (2013.01); *A61Q 1/06* (2013.01); *A61Q 19/00* (2013.01); *C09D 11/00* (2013.01); *C09G 1/14* (2013.01); *C10M 159/12* (2013.01); *C11C 3/00* (2013.01); *C11C 3/003* (2013.01); *C11C 3/02* (2013.01); *C14C 9/02* (2013.01)

(58) Field of Classification Search
CPC ........ A23D 9/00; C07C 57/03; C07C 69/587; C07C 69/33; A01H 5/10; A23L 1/3008; A61Q 19/00; A61Q 1/06; A61Q 1/04; A61Q 1/02; A61Q 1/10; A61Q 17/04; A61Q 19/08; A61Q 19/10; A61K 8/891
USPC ................. 554/161, 162, 170, 173, 224, 227; 424/64, 401; 514/558
See application file for complete search history.

(56) References Cited

U.S. PATENT DOCUMENTS

| | | | |
|---|---|---|---|
| 1,728,205 A | 9/1929 | Hauschka | |
| 2,098,551 A | 11/1937 | Keppler et al. | |
| 4,428,885 A * | 1/1984 | Higaki et al. ................. | 552/544 |
| 5,436,006 A | 7/1995 | Hirose et al. | |
| 8,420,842 B2 * | 4/2013 | Charlier De Chily et al. ............................ | 554/227 |

FOREIGN PATENT DOCUMENTS

| | | | |
|---|---|---|---|
| JP | 01074298 | * | 9/1987 |
| WO | 92 17434 | | 11/1992 |

(Continued)

OTHER PUBLICATIONS

Patent Abstracts of Japan vol. 013, No. 278 (C-611), Jun. 26, 1989 & JP 01 074298 A (Nippon Oil & Fats Co Ltd), Mar. 20, 1989.

(Continued)

*Primary Examiner* — Deborah D Carr
(74) *Attorney, Agent, or Firm* — Oblon, McClelland, Maier & Neustadt, L.L.P.

(57) ABSTRACT

This invention proposes a lanolin substitute, capable of absorbing up to at least twice its weight of water or aqueous solution or aqueous suspension. It forms true emulsions, stable over time with a capacity for water absorption superior to that of lanolin.

It also possesses the known emollient, moisturizing and occlusive properties of lanolin.

This substitute is usable in all the present and future areas of application of lanolin: in the cosmetics industry, dermatology, and in industrial applications (polishes, lubricants . . . ).

It is obtained by hemi-synthesis from a mixture of unsaturated fatty acids, esters of unsaturated fatty acids, unsaturated hydrocarbons or unsaturated derivatives of the latter and compounds comprising or generating hydroxyl functions, such as glycerol, preferably without a catalyst and in an atmosphere devoid of oxygen.

Classical thermal treatment or preferably treatment by dielectric heating.

39 Claims, No Drawings

(56) References Cited

FOREIGN PATENT DOCUMENTS

| WO | 98 04597 | 2/1998 |
| WO | 00 26265 | 5/2000 |

OTHER PUBLICATIONS

Chemical Abstracts, vol. 96, No. 26, Jun. 28, 1982 Columbus, Ohio, US; Abstract No. 223306n, Verbuta, Aneta et al.; Glycedidic emulsidier as a substitute for lanolin and other surfactants p. 380; col. 1; XP002195174 abstract & RO 70 144 A (Intreprinderea De Sapun "Stela") Apr. 8, 1980.

Chemical Abstracts, vol. 95, No. 14, Oct. 5, 1981, Columbus, Ohia, US; abstract No. 117408s, Higaki, Yuzo: "Paste ester hydrate" XP002195175 Abstract & Fureguransu Janaru, vol. 9, No. 1, 1981, pp. 51-55.

Patent Abstracts of Japan, vol. 006, No. 024 (C-091), Feb. 12, 1982 & JP 56 125208 A (Shiseido Co Ltd), Nov. 11, 1981.

\* cited by examiner

LANOLIN SUBSTITUTE, PRODUCTION METHOD THEREOF AND APPLICATIONS OF SAME

CROSS REFERENCE TO RELATED APPLICATION

This application is a continuation of U.S. application Ser. No. 10/481,890, filed on Jan. 2, 2014, which is a 371 of PCT/FR2002/002271, filed on Jun. 28, 2002, and claims priority to French Patent Application No. 01 08905, filed on Jul. 2, 2001.

TECHNICAL SECTOR OF THE INVENTION AND PROBLEM POSED

Lanolin, a fatty substance extracted from the suint of the sheep, is commonly used by the cosmetic and pharmaceutical industries for its emollient, moisturizing, emulsifying properties and its water-absorption capacity.

Despite all these properties, the animal origin of lanolin is less and less satisfactory to the consumer, made uneasy by sheep scrapie. Allergic reactions deriving from pesticide residues, its strong odor, its variable composition, its unreliability of supply, etc. . . . , are additional factors which lead scientists to seek lanolin substitutes.

Attempts at lanolin substitution with oleochemical products are numerous.

The first solution considered consists in re-creating the formula of lanolin, excluding the ingredients of animal origin. The complexity of the composition of lanolin makes this solution difficult: the costs incurred are too high to continue in this way.

A second solution to overcome this problem consists in manufacturing a product with a composition different from that of lanolin but with similar properties.

Until now, the proposed substitutes do not provide full satisfaction because of the properties, the complexity of their composition, certain elevated physico-chemical characteristics such as the acid index, and/or their manufacturing costs.

PRIOR ART

Lanolin
    Composition of Lanolin:
    Lanolin or wool fat is manufactured from the sebaceous secretions of sheep fat. It is a mixture of sterols and long-chain fatty alcohols. This mixture sometimes contains other substances (nickel, chromium, copper . . . ) in the form of traces.
    Its composition is complex, as the following tables show:

TABLE No. 1

| Composition of lanolin (% in wax) | | | |
|---|---|---|---|
| Constituents | % | Constituents after saponification | % |
| Free acids | 0-1 | Fatty acids | 29-38 |
| Esters of triterpenic alcohols and of sterols | 29-44 | α-hydroxy acids | 11-15 |
| Esters of aliphatic alcohols | 14-24 | β-hydroxy acids | 1-3 |
| Monohydroxy esters of sterols, aliphatic and triterpenic alcohols | 15-20 | Polyhydroxy acids | 3-6 |
| Free aliphatic alcohols | 6-20 | Aliphatic alcohols | 5-15 |
| Free triterpenic alcohols and sterols | 4-5 | α-diols | 4-6 |
| Di- and polyhydroxy esters and free diols | 7-9 | Polyols | 3-8 |
| Oxidation derivatives | 2-5 | Cholesterol | 11-20 |
| Hydrocarbons | 0-1 | Lanosterol | 1-8 |
| | | Dihydrolanosterol | 1-5 |
| | | 7-ketacholesta-3,5-diene | 2-4 |
| | | 3-β-hydroxy-7-keto-lanosta-8ene | 1-4 |
| | | Oxidation derivatives | 2-5 |
| | | Hydrocarbons | 0-1 |

T = trace
n = linear
i = isomer
ai = ante-isomer

TABLE No. 2

| Composition of the lanolin carbon chains (% of each constituent) | | | | | |
|---|---|---|---|---|---|
| Chain | Isomers | Fatty acids | α-hydroxy acids | Fatty alcohols | 1-2 alkane diol |
| C10 | n | T | T | — | — |
| | i | T | — | — | — |
| C11 | n | T | T | — | — |
| | ai | 0t1 | — | — | — |
| C12 | n | T | T | T | T |
| | i | 0-1 | T | T | — |
| C13 | n | T | T | — | — |
| | ai | 0-1 | T | — | — |
| C14 | n | 2-4 | 2-3 | T | T |
| | i | 2-5 | T | T | T |
| C15 | n | T | 0-1 | — | — |
| | ai | 3-10 | 0-1 | T | T |
| C16:1 | | 0-1 | — | — | — |
| C16 | n | 4-5 | 62-71 | T | 2-19 |
| | i | 3-11 | 1-2 | 0-1 | 1-2 |
| C17 | n | T | 0-1 | — | T |
| | ai | 3-6 | 0-1 | 1-4 | T |
| C18 | n | 2-4 | 1-3 | 0-1 | 1-4 |
| | i | 4-7 | 8-13 | 0-1 | 20-28 |
| C18:1 | | 0-1 | — | — | — |
| C19 | n | T | 0-1 | — | T |
| | ai | 4-7 | T | 1-3 | 2-5 |
| C20 | n | 0-1 | T | 1-3 | 1-5 |
| | i | 4-7 | 0-1 | 7-18 | 9-12 |
| C21 | n | T | T | T | T |
| C21 | ai | 4-6 | T | 9-25 | 5-10 |
| C22 | n | 0-1 | T | 1-3 | 1-2 |
| | i | 2-3 | 0-1 | 3-6 | 12-22 |
| C23 | n | T | T | T | T |
| | ai | 2-3 | 1-2 | 2-4 | 4-14 |

TABLE No. 2-continued

Composition of the lanolin carbon chains
(% of each constituent)

| Chain | Isomers | Fatty acids | α-hydroxy acids | Fatty alcohols | 1-2 alkane diol |
|---|---|---|---|---|---|
| C24 | n | 2-6 | T | 2-9 | 0-1 |
|  | i | 2-3 | 1-2 | 3-5 | 3-12 |
| C25 | n | T | T | 0-1 | T |
|  | ai | 5-6 | 0-1 | 6-8 | 1-2 |
| C26 | n | 2-5 | T | 1-7 | — |
|  | i | 3-6 | T | 6-13 | 0-1 |
| C27 | n | T | T | T | — |
|  | ai | 3-6 | T | 9-16 | T |
| C28 | n | 1-2 | T | 0-2 | — |
|  | i | 2-3 | T | 1-7 | T |
| C29 | n | T | T | — | — |
|  | ai | 1-4 | T | 2-4 | T |
| C30 | n | 0-1 | T | T | — |
|  | i | 1-3 | T | 1-3 | T |
| C31 | n | T | T | — | — |
|  | ai | 1-4 | — | 0-1 | — |
| C32 | n | T | T | T | — |
|  | i | 0-2 | — | 0-1 | — |
| C33 | n | — | — | — | — |
|  | ai | 0-2 | — | T | — |

Specifications of Lanolin:

Lanolin is a wax, solid, with an amber-yellow color and characteristic odor. It is insoluble in water but soluble in ethanol when hot, ether and chloroform.

The following table compiles the physico-chemical characteristics of this product:

TABLE No. 3 specifications of lanolin

| Characteristics | Lanolin |
|---|---|
| Density at 25° C. | 0.88-0.96 |
| Melting point ° C. | 36-40 |
| Refractive index at 40° C. | 1,480 |
| Acid index | 1-4 |
| Saponification index | 91-118 |
| Iodine index | 20-38 |
| Hydroxyl index | 100-144 |
| Unsaponifiables % | 44-53 |
| Hydrocarbons % | 0-1 |
| Free acids % | 0-1 |
| Total acids % | 48-55 |

Obtaining of Lanolin

Lanolin is extracted from the suint of the sheep, a sebaceous substance secreted by the sweat glands of the animal. The suint represents 15 to 75% of the weight of the wool fibers.

The wool-bearing skin of the killed sheep is sent to the wool stripping industries. At the conclusion of the unhairing operation, the skin and the wool are separated.

The skin is dried and yields the hide which will be sent to the tawery.

For its part, the wool is still greasy; all the suint is on the hair. In order to remove it, the wool is soaked in a bath of soda and soap. It then is ready for the carding (brushing, disentangling) and combing (elimination of short fibers) operations. After refining, the suint is reused in pharmacy and cosmetology.

Principal Producers of Wool:

Nowadays, the wool trade is established principally among the countries exporting untreated wool (particularly Australia and New Zealand) and the countries which are large producers of wool yarns, such as the United States, Italy, Japan and Korea. Only the former USSR and China produce both untreated wool and yarns.

Considerable Decline in the Consumption of Natural Fibers Such as Wool:

Since the neolithic period, wool has been used for the making of textiles. Nonetheless, the ongoing demand for wool products is met in part by synthetic products the qualities of which challenge those of woolen cloths and knitted fabrics, heirs to a long tradition. The artificial fiber share is continually increasing throughout the world (cellulose fibers derived from wood and cotton scrap, polyamides, polyacryls and polyesters, derived from petroleum). In 1990, the chemical fiber industry covered nearly 45% of the world consumption of textile fibers, with 42.5 million tons.

Functions and Applications of Lanolin:

The use of lanolin and its derivatives (acetylated, ethoxylated, hydrogenated, hydroxylated . . . ) is very prevalent in the cosmetics industry and in the industrial sector.

At first lanolin was used in the pharmaceutical sector, in ointments to stabilize the active principles dissolved in water. Then it becomes highly extolled for its emollient and moisturizing properties in formulations.

Cosmetic and Dermatological Functions and Applications

Lanolin is widely used in cosmetics and dermatology for its emollient, moisturizing, emulsifying, occlusive properties. It softens the skin, protects it and prevents its dehydration. Lanolin also has the capacity to absorb up to 4 times its weight in water. In addition, it is not sensitive to oxidation.

The derivatives of lanolin, extremely numerous, obtained through physical or chemical conversion, having better characteristics of odor, color and feel, preferably are used.

Because of its outstanding properties, lanolin and its derivatives figure in the composition of numerous preparations such as: bubble baths, lipsticks, creams, shaving creams, aftershave lotions, powders, soaps, shampoos.

Industrial Functions and Applications

Lanolin also is used in the industrial sector with various applications: waxes, printing inks, anti-rust and anti-corrosion protective films deposited on certain metals, leather and fur industry for waterproofing, paints . . . .

The Reasons for Replacing Lanolin

Despite all its properties, lanolin is criticized more and more for the following reasons:

Its Animal Origin

Today's consumers are more and more concerned about preserving their health and nature. More and more they value the presence of ingredients of vegetable origin in the products they use.

The numerous investigations undertaken on sheep scrapie (TSSE: transmittable subacute spongiform encephalopathy) and mad cow disease (BSE bovine spongiform encephalopathy) worry the consumers, who fear being infected and contracting a variant of Creutzfeldt-Jakob disease (CJD).

Sheep scrapie has been known since the middle of the XVIII century, and it is only in 1985 that the equivalent of this disease of ovines was described in cows. The investigations showed that these cows had been fed with bone meal produced from the carcasses of sheep afflicted with scrapie and without being heated to high temperatures. A disease specific to the sheep therefore is transmitted to the cow which itself can infect humans with CJD.

Its Possible Impurities and The Allergic Reactions

Wool naturally contains impurities such as: grass, soil, abrasive particles and also contaminant substances: pesticides. Even if the wool is cleaned of these impurities before being degreased, traces of pesticides in the lanolin (suint) are not excluded, which deters consumers, concerned about the quality of the products and about their health.

Certain subjects have manifested allergic reactions to cosmetic products containing lanolin not free of pesticide residues and polycyclic alcohols.

Its Strong Odor

Lanolin has a strong characteristic odor which requires the use of a large quantity of scenting agents to mask same. This substantial addition of fragrances is not always well tolerated in persons with sensitive skin.

Its Variable Composition

The composition of lanolin is complex and variable (see Table No. 1). This variability is explained by, among other things, the diversity of species of sheep, their ages, their types of feed, the location. Consequently, it proves difficult to obtain lanolin of consistent quality.

For all these reasons, numerous scientists are seeking to replace lanolin.

The Alternatives for Lanolin Substitution

The first solution considered consists in re-creating the formula of lanolin, excluding the ingredients of animal origin. The complexity of the composition of lanolin (see Tables No. 1 and 2) makes this solution difficult: the costs incurred are too high to continue in this way.

A second solution to overcome this problem consists in manufacturing a product with a composition different from that of lanolin but with similar properties.

Until now, the proposed substitutes do not provide full satisfaction: they are emollient, moisturizing, but they do not have the capacity to absorb water.

In addition, the complexity of their composition, certain elevated physico-chemical characteristics such as the acid index, and/or their manufacturing cost need to be optimized.

Thus there is a considerable and recognized need to find a true lanolin substitute.

SUMMARY OF THE INVENTION

This invention proposes an industrial product new in itself, which constitutes a lanolin substitute and is characterized in that it is capable of absorbing up to at least twice its weight of water or aqueous solution or aqueous suspension. It forms true emulsions, stable over time with a capacity for water retention superior to that of lanolin.

This lanolin substitute is obtained by hemi-synthesis from a mixture of unsaturated fatty acids, esters of unsaturated fatty acids, unsaturated hydrocarbons or unsaturated derivatives of the latter and compounds comprising or generating hydroxyl functions, preferably without a catalyst and in an atmosphere devoid of oxygen.

Applications:

The Applicant has discovered a lanolin substitute for the cosmetic and dermatological market and all the other applications of lanolin, and an original process for preparation.

The applicant has discovered a lanolin substitute for the cosmetic market, and because of its capacity for absorption of water or aqueous solution or aqueous suspension and its emollient, moisturizing properties, it can figure in the composition of numerous preparations.

Examples of Cosmetic Applications:
bubble baths,
lipsticks,
care creams for dry skin,
shaving creams,
aftershave lotions,
powders,
soaps,
shampoos,
waterproof sun creams,
makeup removers,
bath oils,
lip balms,
ointments,
lip wands . . . .

Examples of Industrial Applications:
polishes
printing inks,
anti-rust and anti-corrosion protective films deposited on certain metals,
leather and fur industry for waterproofing,
additives for lubricants,
paints . . . .

This list is not exhaustive. This lanolin substitute can be used in all the present and future applications of lanolin.

The invention pertains in particular, but nonrestrictively, to the thermal treatment of unsaturated fatty acids, esters of unsaturated fatty acids, unsaturated hydrocarbons or unsaturated derivatives of the latter, in variable proportions, with compounds comprising or generating hydroxyl functions, preferably without a catalyst and in an atmosphere devoid of oxygen.

DESCRIPTION OF THE INVENTION

This invention proposes an industrial product new in itself, which is a lanolin substitute, and is characterized in that it is capable of absorbing at least twice its weight of water or aqueous solution or aqueous suspension. It forms true emulsions stable over time with a capacity for water retention superior to that of lanolin.

It also possesses the known emollient, moisturizing and occlusive properties of lanolin. It softens the skin, protects it and prevents its dehydration.

Its manufacturing process is simple and economical as compared with earlier forms.

This lanolin substitute is obtained by hemi-synthesis from a mixture of unsaturated fatty acids, esters of unsaturated fatty acids, unsaturated hydrocarbons or unsaturated derivatives of the latter and compounds comprising or generating hydroxyl functions, preferably without a catalyst and in an atmosphere devoid of oxygen.

The invention pertains to the properties of this product.

In a surprising manner, it has the capacity to absorb up to at least twice its weight of water. Furthermore, the emulsions formed are stable over time and after several passes in an oven at 40° C. This phenomenon is not observed for lanolin which, on the contrary, gives off its water in less than 15 days.

Added to this capacity for absorption of water, the product is emollient, moisturizing, emulsifying and occlusive. It softens the skin, protects it and prevents its dehydration.

The distinctive feature of this invention derives from the addition of reagents comprising or generating hydroxyl functions in the reactional medium. For the sake of simplicity, these reagents will be called "OH-reagents."

The Polymeric Base and its Properties

The Applicant has filed a patent application FR 98 13770 and a patent application PCT WO 00/26265 (PCT/FR99/02646) relating to an original process for dielectric heating. This process applies in particular to the preparation of the lanolin substitute considered here.

According to these patents, the process of polymerization of unsaturated fatty acids, esters of unsaturated fatty acids, unsaturated hydrocarbons, unsaturated derivatives of these compounds, alone or in mixture, is characterized by the fact that the reagent or the reactional mixture is subjected to a dielectric heating to bring about polymerization.

Preferably:

The heating is performed by use of microwave frequencies.

The heating is performed by use o radio frequencies.

It is implemented with or without catalysts.

Heterogeneous or homogeneous catalysts can be added to the reagent or to the reactional mixture.

Catalysts responding to radio frequencies or to microwave frequencies, such as montmorillonite, can be added to the reagent or to the reactional mixture.

The reagent or the reactional mixture, and possibly the catalyst(s), are placed in a batch or discontinuous type reactor adapted for receiving microwave frequencies or radio frequencies.

The reagent or the reactional mixture, and possibly the catalyst(s), are placed in a reactor adapted for performing reactions continuously.

The frequencies range between approximately 30 GHz and approximately 300 MHz.

The frequencies are 2.45 GHz or 915 MHz.

The frequencies range between approximately 300 MHz and approximately 3 MHz.

The frequencies are 13.56 MHz or 27.12 MHz.

The temperature to which the reagent or the reactional mixture, and possibly the catalyst(s) are subjected ranges between 200 and 400° C., preferably between 220 and 350° C.

The time of temperature increase is chosen between 3 and 60 minutes, preferably between 3 and 20 minutes.

The reaction time ranges between 15 minutes and 15 hours, preferably between 15 minutes and 360 minutes, preferably still between 15 and 120 minutes.

The polymerization is performed under an atmosphere which is normal or rich in oxygen or preferably inert; under reduced pressure, preferably between 50 and 10 mm of mercury; while renewing the atmosphere regularly.

The polymerization is stopped by allowing the reagent or the reactional mixture to cool, or by cooling it, to a temperature below the polymerization temperature, depending on the viscosity that one wishes to obtain.

One also may proceed, however, according to a classical thermal treatment.

Without the addition of these "OH reagents," the Applicant obtains with the process set forth hereinabove, polymers of unsaturated fatty acids, esters of unsaturated fatty acids, unsaturated hydrocarbons or derivatives of these products.

These polymers in themselves possess emollient, moisturizing and occlusive properties, extolled for cosmetic formulations. They also have the capacity to absorb water, but this capacity is limited compared to that of lanolin: they absorb up to 80% of their weight of water. The polymeric lattice structure formed is sufficient to accumulate water and form emulsions. Nonetheless, these emulsions are not stable: the water is given off in less than 24 hours.

One technical problem was to make the properties of the polymers obtained come as close as possible to those of lanolin. For this reason, there is added to the reactional medium a sufficient quantity of "OH-reagents," that is, comprising or generating hydroxyl groups.

It was observed in a surprising manner that the products obtained retain the initial properties (emollient, moisturizing, occlusive) but now absorb up to twice their weight of water. In addition, the emulsions formed are stable over time and after several passes in an oven at 40° C. This phenomenon is not observed for lanolin, which gives off all its water in less than 15 days.

These products have a capacity for water retention superior to that of lanolin.

It is to be noted that the addition of OH-reagents comprising or generating hydroxyl groups also makes it possible to reduce the acidity of the products formed by esterification and/or amidification, thus limiting the risks of thermal degradation and hydrolysis reactions. The products formed consequently are far more stable.

Likewise, the addition of OH-reagents into an initial given mixture of unsaturated fatty acids, esters of unsaturated fatty acids, unsaturated hydrocarbons, unsaturated derivatives of the latter, alters the viscosity of the final product.

The Manufacture of these Lanolin Substitutes

The lanolin substitute is obtained by thermal treatment of unsaturated fatty acids, esters of unsaturated fatty acids, unsaturated hydrocarbons, unsaturated derivatives of the latter, or a mixture of these compounds in variable proportion, with one or more OH-reagents comprising or generating hydroxyl functions, preferably without a catalyst and in an atmosphere devoid of oxygen.

The thermal treatment is performed by subjecting the reagents to a classical or dielectric heating as described in the aforementioned patents of the Applicant.

A Classical Thermal Treatment:

The classical thermal treatment is performed between 100 and 400° C. and better still between 230 and 350° C., under ongoing agitation and preferably without a catalyst and under inert atmosphere. The reactional temperature depends on the boiling and/or degradation temperatures of the constituents of the mixture.

The total reaction time depends on the reagent or reagents used and the viscosity that one wishes to obtain. It preferably is between 3 hours and 24 hours, preferably between 3 hours and 10 hours.

B Treatment by Dielectric Heating:

For reasons of gains in time and energy, combined with a lower investment cost, one preferably will use dielectric heating, that is, a heating under microwave frequencies or high frequencies, as described in the aforementioned patents, an abstract of which has been provided hereinabove for the convenience of the individual skilled in the art, and to which the latter usefully may refer for the details of implementation. The individual skilled in the art likewise may refer to the patent application filed on that same day by the Applicant, and relating to an improved piece of equipment for the implementation of dielectric heating.

One preferably proceeds without a catalyst, and it is quite surprising to note that, without a catalyst, an esterification of the free fatty acids is achieved with a reagent product such as glycerol.

It also is very surprising to note that no interfering or competing reactions develop, as was, on the contrary, foreseeable, which perhaps held back research in this manner, and that a good yield therefore is obtained.

The microwave frequencies MW range between approximately 300 MHz and approximately 30 GHz, preferably at 915 MHz (authorized frequency with a tolerance of 1.4%) or at 2.45 GHz (authorized frequency with a tolerance of 2%).

The high frequencies HF range between approximately 3 MHz and approximately 300 MHz, preferably at 13.56 MHz (authorized frequency with a tolerance of 0.05%) or at 27.12 MHz (authorized frequency with a tolerance of 0.6%).

The reaction temperatures are between 100 and 400° C. and better still between 230 and 350° C., under ongoing agitation and preferably without a catalyst and under inert atmosphere. The reactional temperature depends on the boiling and/or degradation temperatures of the constituents of the mixture.

The total reaction time depends on the reagent or reagents used and on the viscosity that one wishes to obtain. It preferably is between 15 minutes and 15 hours, preferably between 15 minutes and 2 hours.

The quantity of OH-reagents added to the reactional mixture depends on the level of water absorption that one wishes to attain for the resulting polymer, as well as on the expected viscosity. The "OH-reagents" can be introduced into the reactional medium at the beginning, during or at the end of reaction.

The addition of these products at the end of reaction generally is not economically advantageous, because the reaction times are increased. However, one may have recourse thereto in certain cases.

The products obtained by this process can undergo additional treatments such as hydrogenation, bleaching, deodorizing or other functionalizations if these treatments impart additional properties such as odor, color . . . .

The Reagents (Classical Thermal Treatment Method or by Dielectric Heating)

For this invention, the reagents may be chosen from among the vegetable oils and fats and from among the polyterpenes, some of which are derived from the said oils and fats.

As oils of vegetable origin there may be mentioned, among others, rapeseed oil, sunflower oil, peanut oil, olive oil, walnut oil, corn oil, soya oil, linseed oil, carthame oil, apricot kernel oil, sweet almond oil, hemp oil, grapeseed oil, copra oil, palm oil, cottonseed oil, babassu oil, jojoba oil, sesame oil, argan oil, thistle oil, squash seed oil, raspberry oil, Karanja oil, Neem oil, poppyseed oil, Brazil nut oil, castor oil, dehydrated castor oil, hazelnut oil, wheatgerm oil, borage oil, evening primrose oil, Tung oil, tall oil.

These oils and fats of vegetable origin, as well as their derivatives, can undergo a preliminary treatment intended to make them more reactive or, on the contrary, less reactive. The invention likewise relates to an isolated reagent as well as to a reactional mixture comprising two or more components. These reactional mixtures may comprise equivalent proportions of each component or certain components may be predominant.

As unsaturated hydrocarbons there may be cited, alone or in mixture, and by way of nonrestrictive examples, an alkene, for example one or more terpenic hydrocarbons, that is, one or more isoprene polymers, or one or more isobutene, styrene, ethylene, butadiene, isoprene, propene polymers, or one or more copolymers of these alkenes.

As unsaturated fatty acids there may be used, alone or in mixture, and by way of nonrestrictive examples, one or more monounsaturated fatty acids such as oleic acid, palmitoleic acid, myristic acid, petroselenic acid, erucic acid; one or more polyunsaturated fatty acids such as, for example, linoleic acid, the alpha and gamma linolenic acids, arachidonic acid; one or more acids comprising conjugated dienes or conjugated trienes such as licanic acid, the isomers of linoleic and linolenic acids; one or more acids comprising one or more hydroxyl groups such as ricinoleic acid.

As esters of unsaturated fatty acids there may be used, alone or in mixture and by way of nonrestrictive examples, one or more of the esters obtained by esterification between a monoalcohol and/or polyol and at least one unsaturated fatty acid; waxes; phospholipids; sphingolipids; glucolipids.

The oils and fats of vegetable origin, the hydrocarbons as well as their derivatives can undergo a preliminary treatment intended to make them more reactive or, on the contrary, less reactive, such as, for example, hydrogenation, hydroxylation, epoxidation, phosphitation, sulfonation.

Although the oils and fats of animal origin preferably are not used, there can be cited, among others, sperm whale oil, dolphin oil, whale oil, seal oil, sardine oil, herring oil, shark oil, codliver oil, ox foot oil, lard, horse fat.

For this invention, the OH-reagents comprising or generating hydroxyl functions can be chosen from among the alcohols, the aminoalcohols, the epoxides.

As alcohols, there may be used, alone or in mixture, one or more primary, secondary and/or tertiary mono- or polyalcohols. By way of nonrestrictive examples, methanol, ethanol, butanol, glycerol, glycol, sorbitol, mannitol, xylitol, neopentylglycol, pentaerythritol, vitamins (for example tocopherol, ascorbic acid, retinol), sterols (including the phytosterols), hemiacetals (for example 1-ethoxy-1-ethanol) and their analogues may be involved.

As aminoalcohols, there may be used, alone or in mixture and by way of nonrestrictive examples, monoethanolamine MEA, diethanolamine DEA, triethanolamine TEA, 3-amino 1,2 propanediol, 1-amino 2-propanol, 2-2'-amino ethoxy ethanol.

As epoxides, there may be used, alone or in mixture and by way of nonrestrictive examples, 1,2-epoxy-9-decene, 3-4 epoxy-1-butene, 2-3 epoxy-1-propanol, fatty esters obtained by esterification between 2-3 epoxy-1-propanol and a fatty acid (for example Cardura E10®).

The alcohols, the aminoalcohols, the epoxides as well as their derivatives can undergo a preliminary treatment intended to make them more reactive or, on the contrary, less reactive, such as, for example, hydrogenation, hydroxylation, epoxidation, phosphitation, sulfonation.

Among the catalysts or additives, there shall be understood by way of nonrestrictive examples the usual acid catalysts (paratoluenesulfonic acid, sulfuric acid, phosphoric acid, perchloric acid . . . ), the usual basic catalysts (soda, potassium hydroxide, alcoholate of alkaline metals and of alkaline-earth metals, sodium acetate, triethylamines, derivatives of pyridine . . . ), the acid and/or basic resins of the Amberlite™, Amberlyst™, Purolite™, Dowex™, Lewatit™ type, the zeoliths and the enzymes, the carbon blacks and the activated carbon fibers.

The invention relates to a process characterized in that there is added from 0.1 to 30%, preferably from 0.1 to 6% of "OH-reagent," preferably 1 or 3%, in particular from 0.1 to 5, preferably 1 or 3% of glycerol, and the OH reagent is chosen from among glycerol, sorbitol, MEA, polyglycerol, vitamin C or E.

Concrete but nonrestrictive examples of the invention now are going to be presented.

EXAMPLES

The following examples make it possible to demonstrate the fact that the water-absorption capacity of the polymeric base, formed from a mixture of unsaturated fatty acids, esters of unsaturated fatty acids, unsaturated hydrocarbons or unsaturated derivatives of the latter, is increased by adding to the reactional medium compounds comprising or generating hydroxyl functions.

I—Water Absorption

1—Protocols for Placement in Emulsion

The tests for water-absorption capacity are performed in two ways:

1-placement in emulsion, heating at 60° C. with the aid of a bar magnet (protocol No. 1)

2—Placement in emulsion, heating at 60° C. with the aid of a turbine paddle (protocol No. 2)
   a—protocol No. 1
Equipment Required:
   250 mL beakers
   magnetic stirrer with heating plate
   50 mL burette
Protocol:
   weigh out a mass m1 of lanolin substitute into a beaker
   heat the product to 60° C. under agitation (bar magnet) with the aid of a heating apparatus
   add cold water dropwise with the aid of a graduated burette until the product no longer absorbs it
   note the mass m2 of the absorbed water
   evaluate the absorption capacity (m2/m1*100)
   periodically monitor the stability of the emulsion
   This protocol makes it possible to have a good idea of the efficacy of the products.
   b—protocol No. 2
   Protocol No. 2 is more precise and more complete than protocol No. 1.
Equipment Required:
   stainless steel beakers (100-250-500 mL)
   water-bath
   HEIDOLPH stirrer, 280-2200 rpm (scale from 0 to 10) with deflocculant turbine
   pipettes
   spatula
   METTLER TOLEDO pHmeter MP220
   HETTICH UNIVERSAL centrifuge (4000 U/min at 100%)
Reagents Required:
   1 to 0.1% blue aqueous solution
   Kathon CG solution
   pH=7 and 4 and 11 solution
Protocol:
   1—weigh out the oil into a 500 mL beaker (m1)
   2—heat the oil in a water-bath at 60° C.
   3—stir at 4
   4—weigh out the water (m2, here 200%) into a 250 mL stainless steel beaker
   5—add into the water 3 drops of blue solution and 3 drops of Kathon CG
   6—heat the water in another water-bath at 80° C. (thermometer)
   7—add the water dropwise with the aid of a pipette
   8—once the emulsion is set, quickly add the remaining water, while stirring at 6
   9—wait 5 minutes after addition for the emulsion to be completed
   10—cool the emulsion in a bath of cold water while stirring with the spatula
   11—check the conductivity of the emulsion with the standardized pHmeter
   12—centrifuge for 15 min at 4000 U/min (100%)
   13—once it is finished, observe the dephasing or lack thereof (revealed by the blue solution)
   14—perform tests for stability over time by a pass in an oven at 40 and 50° C.
   c—Legend:
CAE (1)=water-absorption capacity obtained by following protocol No. 1, expressed in %
CAE (2)=water-absorption capacity obtained by following protocol No. 2, expressed in %
S(1)=stability of the emulsion obtained by following protocol No. 1, expressed in days
S(2)=stability of the emulsion obtained by following protocol No. 2, expressed in days
R(2)=giving-off of water after pass in the centrifuge, expressed by yes/no
2—Influence of Addition of Glycerol and of Viscosity on the Water-Absorption Capacity The products which appear in the tables hereinbelow are obtained from the thermal treatment of the same unsaturated fatty acids and/or esters of unsaturated fatty acids and/or unsaturated hydrocarbons and/or unsaturated derivatives of the latter.

Only the proportions of each compound in the mixture vary, so as to obtain the desired viscosity at the end of synthesis.

TABLE No. 5

| lanolin | | |
|---|---|---|
| Reference | CAE (2) | S(2) at 25° C. |
| Lanolin | >200 | stable |

The objective is to achieve these two criteria: a water-absorption capacity in excess of 200% and a stability over time for the emulsion formed.

TABLE No. 6

| Viscosities of the polymeric bases without glycerol | | | |
|---|---|---|---|
| 0% GLYCEROL | VISCOSITY cP (40° C.) | CAE (1) | S(1) at 25° C. |
| CM137/00 | 600 | 80 | <1 day |
| CM34/01 | 1800 | 70 | <1 day |
| CM120/00, CM121/00 | 2500 | 80 | <1 day |
| CM113/00, CM87/00 | 4500 | 80 | <1 day |
| CM91/00 | 10000 | 42 | <1 day |

Without the addition of OH-reagents, the polymers of unsaturated fatty acids, esters of unsaturated fatty acids, unsaturated hydrocarbons or derivatives of these products absorb up to 80% of their weight of water.

The polymeric lattice structure formed makes it possible to accumulate the water.

The water-absorption capacity is limited, however, compared with that of lanolin. In addition, the water is given off in less than one day.

It also is important to note that the water penetrates complex polymeric lattices with difficulty (example: CM91/00).

TABLE NO. 7

| Viscosities of lanolin substitutes obtained with 3% glycerol | | | | | | |
|---|---|---|---|---|---|---|
| 3% GLYCEROL | VISCOSITY cP (40° C.) | CAE (1) | CAE (2) | R(2) | S(1) 25° C. | S(2) 25° C. |
| CM76/01 | 600 | 170 | >200 | no | 15 days | 15 days |
| CM78/01 | 1000 | 280 | >200 | no | 30 days | stable |
| CM80/01 | 1800 | 280 | >200 | no | stable | stable |
| CM81/01 | 2500 | 295 | >200 | no | stable | stable |
| CM82/01 | 4500 | 200 | >200 | no | stable | stable |
| CM99/01 | 10,000 | 200 | >200 | no | stable | stable |

The glycerol is added into the initial mixture prior to beginning the synthesis.

The products obtained then absorb up to at least twice their weight of water.

The emulsions formed are stable at room temperature except for the non-viscous products (600 and 1000 cP at 40° C.). In order for the latter to be stable, it is necessary to reduce the quantity of water absorbed. Their water-absorption capacity is between 80 and 200%.

The choice of product and of its viscosity depends on the desired application and effect. The more viscous the product, the thicker the emulsion obtained.

3—Stability of the Emulsions

The emulsions formed undergo different "oven at 40° C.-centrifuge" cycles to control their stability.

The results obtained appear in the table hereinbelow:

TABLE No. 8 stability test with oven at 40° C.

| 3% GLYCEROL | VISCOSITY cP (40° C.) | CAE (2) | S(2) 25° C. | S(2) CYCLES |
|---|---|---|---|---|
| CM76/01 | 600 | >200 | 15 days | 15 days |
| CM78/01 | 1000 | >200 | stable | stable |
| CM80/01 | 1800 | >200 | stable | stable |
| CM81/01 | 2500 | >200 | stable | stable |
| CM82/01 | 4500 | >200 | stable | stable |
| CM99/01 | 10,000 | >200 | stable | stable |
| Lanolin | — | >200 | stable | 15 days |

The products with viscosity in excess of 1000 cP (at 40° C.) absorb more than twice their weight of water and form true emulsions.

These emulsions are stable, unlike lanolin which gives off all its water in 15 days after a pass in an oven at 40° C.

These lanolin substitutes therefore have a water-absorption capacity equivalent to that of lanolin, but the capacity for retention thereof is better.

4—Influence of Percentage of Glycerol

The products which appear in the table hereinbelow are obtained from the thermal treatment of the same mixture of unsaturated fatty acids and/or esters of unsaturated fatty acids and/or unsaturated hydrocarbons and/or unsaturated derivatives of the latter (nature of products and proportions identical).

Only the quantity of glycerol introduced into the mixture varies.

TABLE No. 9 water-absorption capacity as a function of the percentage of glycerol added

| PRODUCT NAME | % GLYCEROL | VISCOSITY cP 40° C. | CAE (1) | S(1) |
|---|---|---|---|---|
| CM20/01 | 0 | 900 | 80 | <1 day |
| CM28/01 | 1 | 850 | 80 | <1 day |
| CM38/01 | 3 | 500 | 170 | <15 days |
| CM29/01 | 5 | 450 | 190 | <15 days |

The water-absorption capacity increases with the percentage of glycerol.

The emulsions formed are not stable. As before, the products are not sufficiently viscous: the polymeric base does not provide enough substance.

It is to be noted that the viscosity of a given mixture decreases with the percentage of glycerol.

5—Comparison of Water-absorption Capacities of Different Reagents

The products which appear in the table hereinbelow are obtained from the thermal treatment of the same mixture of unsaturated fatty acids and/or esters of unsaturated fatty acids and/or unsaturated hydrocarbons and/or unsaturated derivatives of the latter (nature of products and proportions identical).

Only the compound comprising or generating the hydroxyl functions changes. The quantity to be added to the reactional medium varies as a function of the hydroxyl functions of the OH-reagent which are able to react during the synthesis and those which do not react for reasons of steric obstruction.

TABLE NO. 10 water-absorption capacity of different OH-reagents

| OH-reagent | glycerol | polyglycerol | polyglycerol | sorbitol | sorbitol | MEA |
|---|---|---|---|---|---|---|
| %/mixture | 3% | 3% | 30% | 3% | 6% | 6% |
|  | CM110/01 | CM118/01 | CM121/01 | CM111/01 | CM113/01 | CM114/01 |
| % water | 240 | 220 | 80 (L) | 150 | 187 | 162 |

| OH-reagent | Vitamin C | Vitamin E |
|---|---|---|
| %/mixture | 3% | 6% |
| Product | CM117/01 | CM115/01 |
| % water | 90 | 120 |

Comment: the product CM121/01 does not yield a true emulsion. It absorbs only 80% of its weight of water and the mixture obtained (CM121/01 + water) is liquid.

II—Formulations

1—Emollient, Moisturizing and Occlusive Properties of a Sunflower Oil Polymerized Without OH The Applicant has filed a patent application FR 98 13770 and a patent application PCT WO 00/26265 (PCT/FR99/02646).

In this patent, he shows the advantages of a care cream for the hands formulated by replacing all or part of the ingredients with a polymerized sunflower oil (HTP)

TABLE No. 11

Formula for a care cream for the hands

| COMPONENT | FUNCTION | Initial formula % | Modified formula % |
|---|---|---|---|
| HTP | Substitute | 0 | 5 |
| Stearic alcohol | Emulsifier | 5 | 4 |

TABLE No. 11-continued

Formula for a care cream for the hands

| COMPONENT | FUNCTION | Initial formula % | Modified formula % |
|---|---|---|---|
| Stearic acid | Emulsifier | 0.4 | 0.2 |
| Shea butter | Emollient/Emulsifier | 1 | 0 |
| Water | | 66.6 | 73.8 |
| Glycerin | "Emulsifying" moisturizer | 20 | 10 |
| Other ingredients | Various additives | 7 | 7 |

The benefits of the modified formula are the following:
It lathers less on application;
It is more emollient (it softens the skin);
It forms a barrier which protects the hydration of the skin.
The polymerized sunflower oil is advantageous for the formulator of cosmetic products because:
  The emollient capacity of the formula is superior while the proportion of water has been increased;
  The HTP has a viscosity-imparting capacity;
  The HTP is a coemulsifier (thickener)

2—Applications with Emulsions

The table hereinbelow describes the formula of a multipurpose nutritive cream:

TABLE No. 12

Formula for a multipurpose nutritive cream

| Ingredients | Control | CM68/00 | CM72/00 | CM81/00 |
|---|---|---|---|---|
| Demineralized water | QSP 100 | QSP 100 | QSP 100 | QSP 100 |
| Glycerin | 15 | 15 | 15 | 15 |
| Triethanolamine | 0.67 | 0.67 | 0.67 | 0.67 |
| Vaseline | 8 | 8 | 8 | 8 |
| Glyceryl Stearate | 6 | 6 | 6 | 6 |
| Stearic acid | 3 | 3 | 3 | 3 |
| Vaseline oil | 2 | 2 | 2 | 2 |
| Dimethicone | 0.85 | 0.85 | 0.85 | 0.85 |
| Cyclomethicone | 2.5 | 2.5 | 2.5 | 2.5 |
| Preservative | 0.5 | 0.5 | 0.5 | 0.5 |
| Vitamin E acetate | 0.05 | 0.05 | 0.05 | 0.05 |
| Vitamin A palmitate | 0.1 | 0.1 | 0.1 | 0.1 |
| Carbomer | 0.24 | 0.24 | 0.24 | 0.24 |
| Lanolin alcohols | 2 | 0 | 0 | 0 |
| CM68/00 (600 cP at 40° C.) | 0 | 2 | 0 | 0 |
| CM72/00 (600 cP at 40° C.) | 0 | 0 | 2 | 0 |
| CM81/00 (2500 cP at 40° C.) | 0 | 0 | 0 | 2 |

The formulations based on the products CM68/00 and CM72/00 provide advantageous cosmetic properties as compared with the control:
  rapid penetration despite a slightly less satisfactory application.
  final velvety sensation on the skin.
  reduced oily sensation.

3—Other Applications a—Ointment

| Control ointment | Aldivia ointment | Quantity (%) |
|---|---|---|
| Vaseline | Vaseline | 50 |
| Lanolin | CM82/01 (v = 4500 cP, 3% glycerol) | 30 |
| Beeswax | Beeswax | 5 |
| Neem oil | Neem oil | 5 |
| Stabilized shea butter | Stabilized shea butter | 10 | b—Lipstick

| Control stick | Quantity (%) | Aldivia Stick | Quantity (%) |
|---|---|---|---|
| Vaseline | 58.7 | Vaseline | 29.35 |
| | | CM82/01 (v = 4500 cP, 3% glycerol) | 29.35 |
| Paraffin 52/54 | 10 | Paraffin 52/54 | 10 |
| Cerozo E626 | 10.5 | Cerozo E626 | 10.5 |
| Cerewax A75 | 10.5 | Cerewax A75 | 10.5 |
| Crodamol ML | 10 | Crodamol ML | 10 |
| Vitamin E acetate | 0.1 | Vitamin E acetate | 0.1 |
| Propylparaben | 0.2 | Propylparaben | 0.2 |

CONCLUSION

These examples show the efficacy of these products: they constitute true lanolin substitutes.

They have the capacity to absorb up to at least twice their weight of water and their retention capacity is superior to that of lanolin.

Like lanolin, they are emollients, moisturizers and occlusives. They soften the skin, protect it and prevent its dehydration.

The choice of product and of its viscosity depends on the desired application and effect. The more viscous the product is and forms a polymeric lattice, the thicker and more stable over time the emulsion obtained.

The quantity of OH-reagents added to the medium depends on the water-absorption capacity desired.

The invention also relates to all the embodiments and variants directly accessible to the individual skilled in the art.

The invention claimed is:

1. A lanolin substitute, comprising a polyglyceride comprising monomer units of an unsaturated fatty acid, an ester of an unsaturated fatty acid, an unsaturated hydrocarbon, or a combination thereof and monomer units of glycerol, wherein the lanolin substitute is capable of absorbing twice its weight of any of water, an aqueous solution or an aqueous suspension.

2. The lanolin substitute according to claim 1, wherein the polymer has a polymeric lattice structure.

3. A cosmetic, dermatological or industrial-use formulation, comprising at least one lanolin substitute according to claim 1.

4. A method of making the lanolin substitute according to claim 1, comprising heating a mixture comprising glycerol and at least one of an unsaturated fatty acid, an ester of an unsaturated fatty acid, an unsaturated hydrocarbon, and an unsaturated derivative of the hydrocarbon, to form the polyglyceride.

5. The method according to claim 4, wherein the heating of the mixture comprises hemi-synthesis from a mixture comprising glycerol and at least one of an unsaturated fatty acid, an ester of an unsaturated fatty acid, an unsaturated hydrocarbon, and an unsaturated derivative of the hydrocarbon.

6. The method according to claim 4, wherein the heating of the mixture comprises subjecting the mixture to a dielectric heating.

7. The method according to claim 6, wherein the dielectric heating is carried out with one or more microwave frequencies or radio frequencies.

8. The method according to claim 6, wherein the mixture further comprises at least one catalyst.

9. The method according to claim 6, wherein the heating of the mixture is conducted in the presence of one or more of heterogeneous or homogeneous catalyst added to the mixture.

10. The method according to claim 6, wherein the heating is carried out in a batch or discontinuous reactor adapted for receiving microwave frequencies or radio frequencies.

11. The method according to claim 6, wherein the heating is carried out in a reactor adapted for performing reactions continuously.

12. The method according to claim 7, wherein the dielectric heating is carried out with one or more frequencies ranging from approximately 30 GHz to approximately 300 MHz or from approximately 300 MHz to approximately 3 MHz.

13. The method according to claim 6, wherein the temperature at which the mixture is heated ranges from 200 and 400° C.

14. The method according to claim 6, wherein the heating comprises increasing the temperature for between 3 and 60 minutes.

15. The method according to claim 6, wherein the heating is carried out for between 15 minutes and 15 hours.

16. The method according to claim 4, wherein the heating is a classical thermal treatment.

17. The method according to claim 16, wherein the classical heating is carried out between 100 and 400° C. under ongoing agitation.

18. The method according to claim 16, wherein the heating is carried out for between 3 hours and 24 hours.

19. The method according to claim 10, wherein the heating is carried out in the absence of a catalyst.

20. The method according to claim 4, wherein the glycerol is introduced into the mixture at the beginning, during or at the end of said heating.

21. The method according to claim 4, further comprising at least one of hydrogenating, bleaching and deodorizing the lanolin substitute.

22. The method according to claim 4, wherein the mixture comprises one or more of a vegetable oil, a fat or a polyterpene.

23. The method according to claim 22, wherein the mixture comprises an oil or fat selected from the group consisting of rapeseed oil, sunflower oil, peanut oil, olive oil, walnut oil, corn oil, soya oil, linseed oil, carthame oil, apricot kernel oil, sweet almond oil, hemp oil, grapeseed oil, copra oil, palm oil, cottonseed oil, babassu oil, jojoba oil, sesame oil, argan oil, thistle oil, squash seed oil, raspberry oil, Karanja oil, Neem oil, poppyseed oil, Brazil nut oil, castor oil, dehydrated castor oil, hazelnut oil, wheatgerm oil, borage oil, evening primrose oil, Tung oil, and tall oil.

24. The method according to claim 22, wherein the mixture further comprises one or more isolated reagent.

25. The method according to claim 4, wherein the mixture comprises at least one an unsaturated fatty acid selected from the group consisting of oleic acid, palmitoleic acid, myristic acid, petroselenic acid, erucic acid, linoleic acid, alpha linolenic acid, gamma linolenic acid, arachidonic acid, licanic acid, an isomer of linoleic acid, an isomer of linolenic acid, and ricinoleic acid.

26. The method according to claim 4, wherein the mixture comprises an ester of an unsaturated fatty acid obtained by esterification of at least one of a monoalcohol or a polyol and at least one of an unsaturated fatty acid, a wax, a phospholipid, a spingolipid, or a glucolipid.

27. The method according to claim 4, wherein the mixture comprises one or more of an oil or a fat of vegetable origin, a hydrocarbon, or a derivative of a hydrocarbon, treated by at least one of hydrogenation, hydroxylation, epoxidation, phosphitation, or sulfonation.

28. The method according to claim 4, wherein the mixture comprises one or more oils or fats selected from the group consisting of sperm whale oil, dolphin oil, whale oil, seal oil, sardine oil, herring oil, shark oil, codliver oil, ox foot oil, lard, and horse fat.

29. The method according to claim 4, wherein the mixture further comprises at least one of an acid catalyst selected from the group consisting of paratoluenesulfonic acid, sulfuric acid, phosphoric acid, and perchloric acid; a basic catalyst selected from the group consisting of soda, potassium hydroxide, an alcoholate of alkaline metal, an alcoholate of alkaline-earth metal, sodium acetate, triethylamine, and a derivative of pyridine; an acid resin; a basic resin; a zeolith; an enzyme; carbon black; and an activated carbon fiber.

30. The method according to claim 4, wherein the glycerol is present in the mixture in an amount of from 0.1 to 5%, relative to the total amount of the mixture.

31. The method of claim 4, wherein the thermal treatment is carried out in the absence of a catalyst and in an atmosphere devoid of oxygen.

32. The method according to claim 9, wherein the catalyst is montmorillonite.

33. The method according to claim 6, wherein the temperature at which the mixture is heated is between 220 and 350° C.

34. The method according to claim 6, wherein the temperature at which the mixture is thermally treated is increased for between 3 and 20 minutes.

35. The method according to claim 6, wherein the thermal treatment is carried out for between 15 and 360 minutes.

36. The method according to claim 6, wherein the heating is carried out for between 15 and 120 minutes.

37. The method according to claim 16, wherein the classical heating is carried out at a temperature of between 230 and 350° C. under ongoing agitation.

38. The method according to claim 16, wherein the heating is carried out in the absence of a catalyst under an inert atmosphere.

39. The lanolin substitute of claim 5, wherein the heating is carried out in the absence of a catalyst and in an atmosphere devoid of oxygen.

* * * * *